United States Patent [19]

Marcelli

[11] 4,106,911
[45] Aug. 15, 1978

[54] DEVICE FOR EXAMINING A PLURALITY OF MICRODOSES OF LIQUIDS

[75] Inventor: Aline Marcelli, Paris, France

[73] Assignee: Societe Francaise pour le Developpement de l'Automatisme en Biologie, Paris, France

[21] Appl. No.: 811,298

[22] Filed: Jun. 29, 1977

[30] Foreign Application Priority Data

Jul. 9, 1976 [FR] France .................................. 76 21013
Feb. 2, 1977 [FR] France .................................. 77 02846

[51] Int. Cl.² .......................... G01N 1/14; G01N 1/18
[52] U.S. Cl. ..................................... 23/259; 73/425.6; 141/237; 141/238; 141/284; 195/127
[58] Field of Search ............... 23/230 R, 253 R, 259, 23/292; 195/127, 139; 141/284, 237, 238; 73/425.6

[56] References Cited

U.S. PATENT DOCUMENTS

| 3,568,735 | 3/1971 | Lancaster | 23/259 |
| 3,607,097 | 9/1971 | Auphan | 23/253 R |
| 3,650,306 | 3/1972 | Lancaster | 23/259 X |
| 3,883,308 | 5/1975 | Matte | 23/253 R |

Primary Examiner—R.E. Serwin
Attorney, Agent, or Firm—Merriam, Marshall & Bicknell

[57] ABSTRACT

A device for examining a plurality of microdoses of liquids by means of a plurality of reagents, said device comprising in combination a dispenser for dispensing microdoses of reagents, comprising a plurality of vertical syringes adapted to be controlled simultaneously and arranged in a fixed pattern, a means for filling said syringes with reagents, provided with a plurality of receptacles containing said reagents and arranged in a fixed pattern corresponding to the pattern of said syringes, a receptacled assembly wherein a plurality of reaction receptacles are arranged in a fixed pattern likewise corresponding to the pattern of said syringes, and a dispenser for dispensing microdoses of liquids. The invention finds application in the testing of liquids, particularly in the field of cytology and immuno-haematology.

7 Claims, 10 Drawing Figures

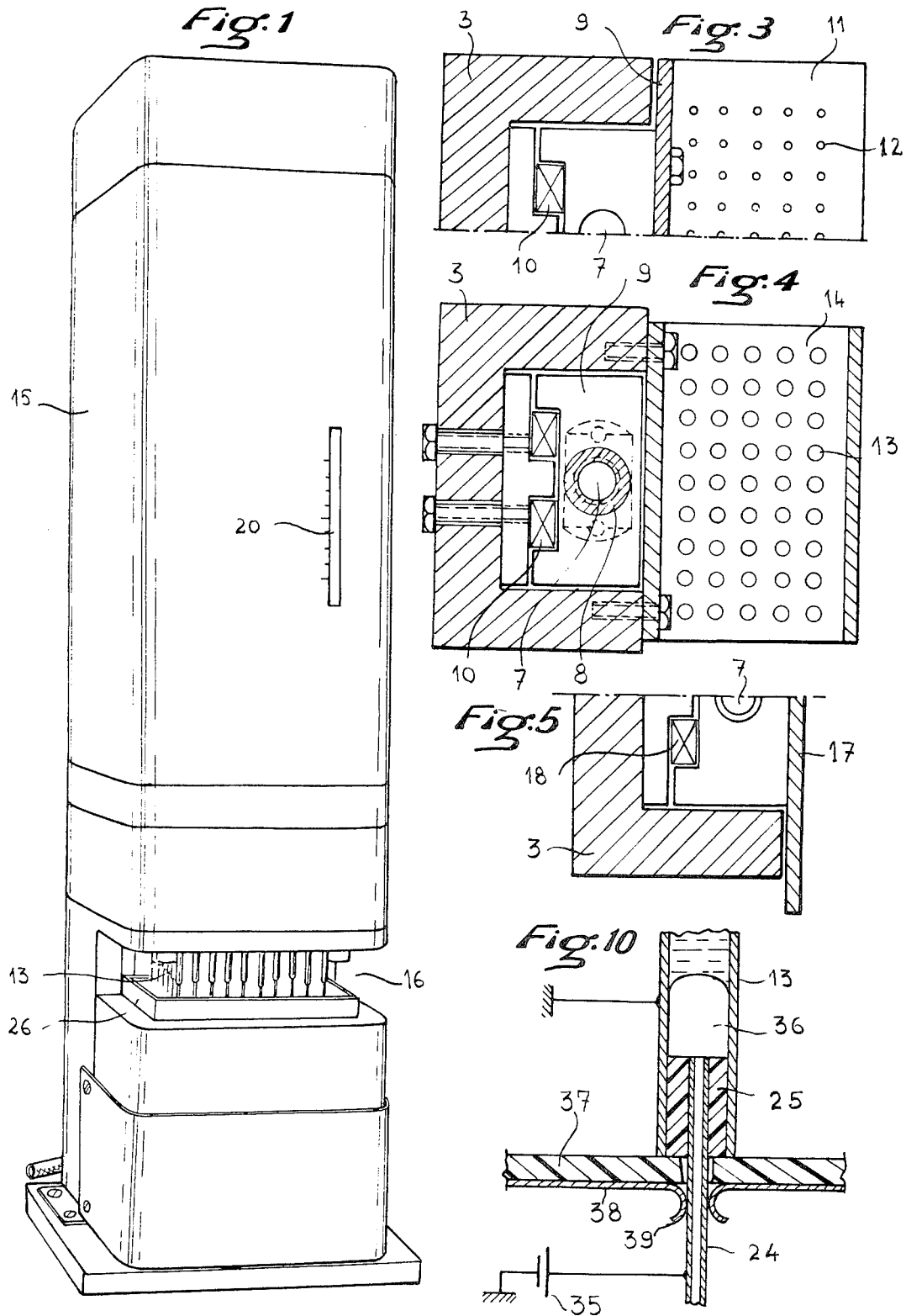

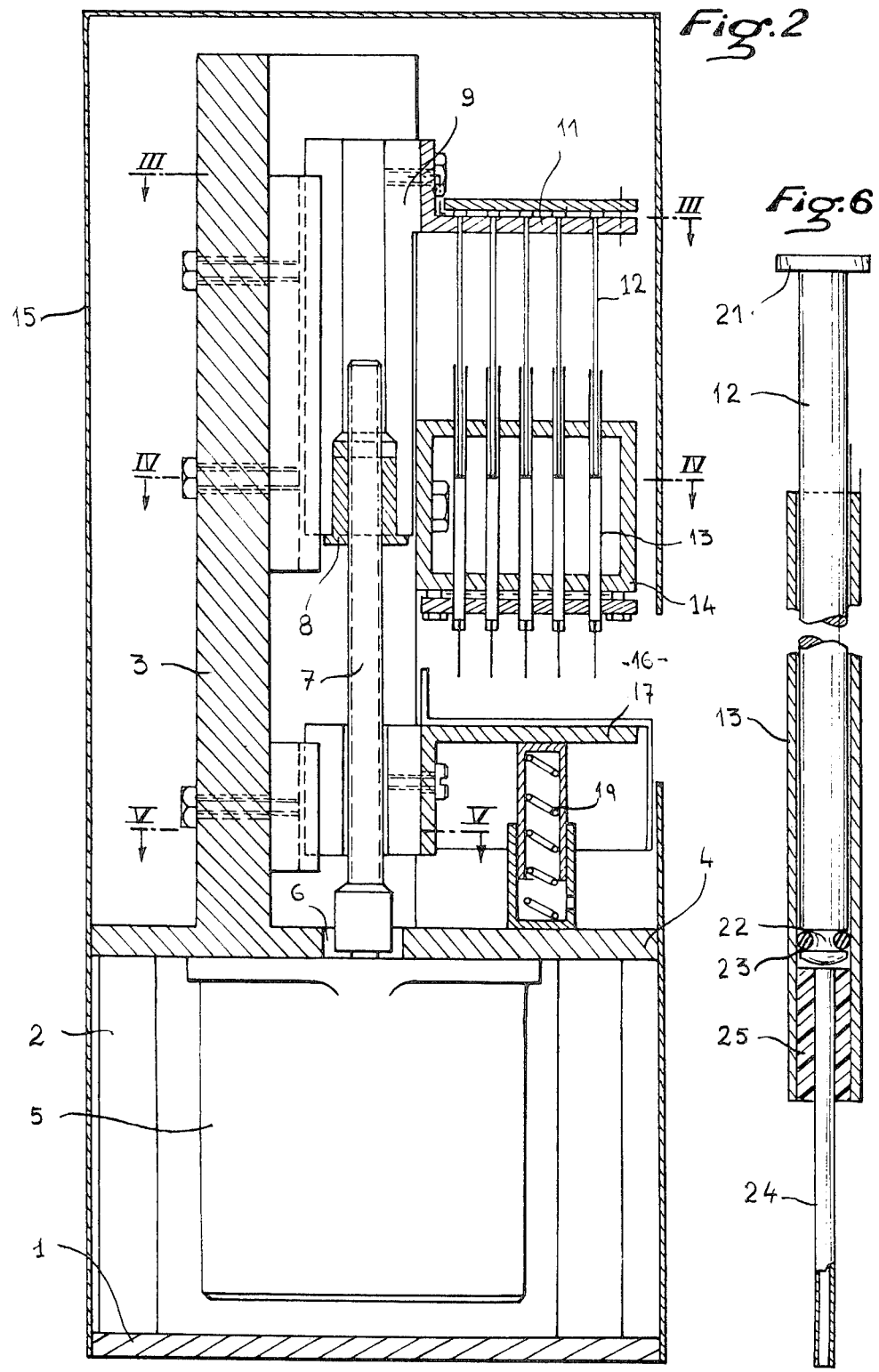

DEVICE FOR EXAMINING A PLURALITY OF MICRODOSES OF LIQUIDS

The present invention relates to a device for examining a plurality of microdoses of liquids by means of a plurality of reagents. This device is particularly, but not exclusively, applied to microtests made on erythrocytes, leucocytes or on other cellular or microbial elements, possibly with display of the reactions on a video screen, and simultaneous display of the results. The device has numerous applications in the examination of serological and biochemical liquids, particularly in the field of cytology and immuno-haematolgogy.

The device according to the invention comprises, in combination, a dispenser for dispensing microdoses of reagents comprising a plurality of vertical syringes adapted to be controlled simultaneously and arranged in a fixed pattern, a means for filling said syringes with reagents provided with a plurality of receptacles containing said reagents and arranged in a fixed pattern corresponding to the pattern of said syringes, a receptacles assembly wherein a plurality of reaction receptacles are arranged in a fixed pattern likewise corresponding to the pattern of said syringes, and a dispenser for dispensing microdoses of liquids.

In the reagent dispenser, all the bodies of the syringes are advantageously made fast with a first member, whilst all the plunger rods of the syringes are made fast with a second member, one of said first or second members being mounted to move vertically with respect to the other, preferably under the action of an electric motor with step-by-step functioning at least in the direction of dispensing of the doses.

When the bodies of the syringes are fixed and when the rods of the plungers are mobile, the reagent dispenser may comprise, beneath the needles of the syringes, a support for the reagent-filling means and for the receptacled assembly. The microdose dispenser will advantageously comprise a frame provided with a vertical arm and containing an electric motor actuating a likewise vertical screw, said arm serving as guide for the mobile member which is fast with a nut cooperating with said screw.

Of course, the liquid dispenser may be similar to, or different from, the reagent dispenser.

The syringes of the microdose dispenser are preferably made entirely of stainless steel. For example, the plunger may be constituted by a rod provided with an annular groove in which is disposed an O-ring serving as seal with the syringe body, which may be formed by a tube, the needle itself being constituted by a tube of smaller diameter and the seal between the syringe body and the needle being effected by means of an electrically insulating material. In this way, if a (minimum) potential difference is applied between said body and said needle, it is possible to detect, by the variation in conductivity, the presence of an air bubble inside, near the needle, and therefore the level of reagent in the syringe. To this end, a printed circuit may be provided, disposed beneath said syringes and through which pass the needles thereof, and comprising printed conductors in contact with said needles.

The means for filling the syringes with reagents advantageously also serves to package said reagents and to this end it may comprise a lid hermetically covering the assembly to close the receptacles.

The receptacled assembly, at least as far as the bottom of its receptacles is concerned, is preferably constituted by a transparent material. Moreover, each receptacle bottom is flat. In this way, it is possible to observe the result of the reactions (for example the formation of agglutinates) through said bottom, for example by means of a television camera, reproducing the magnified image on a video screen. To this end, the receptacles are at least approximately cylindrical.

The invention will be more readily understood on reading the following description with reference to the accompanying drawings, in which:

FIG. 1 is a perspective view of the dispenser for dispensing micro-doses of reagents and/or of analysed liquids according to the invention.

FIG. 2 is a schematic longitudinal section through the dispenser of FIG. 1.

FIGS. 3, 4 and 5 are sections corresponding to lines III—III, IV—IV and V—V of FIG. 2, respectively.

FIG. 6 shows a longitudinal section of a syringe for the dispenser of FIG. 2.

Figure 7:
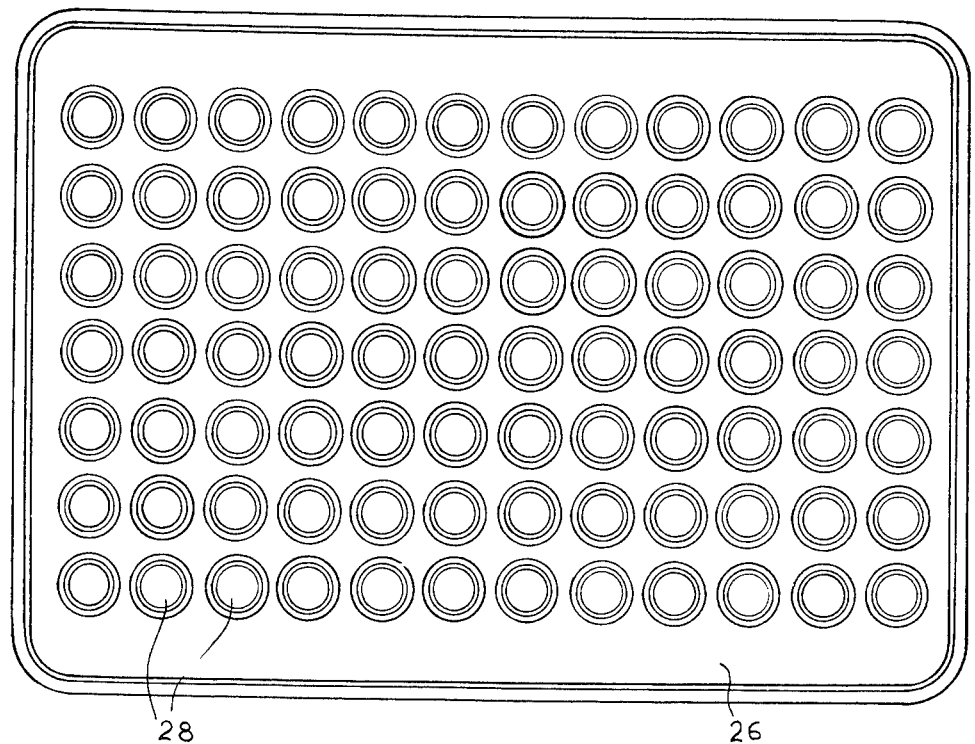
FIG. 7 is a plan view of the receptacled assembly according to the invention, the lid having been removed.

FIG. 10 schematically illustrates the device for detecting air bubbles near the needle of the syringes.

Referring now to the drawings, FIGS. 1 and 2 show the dispenser of micro-doses of reagents and/or liquids according to the invention, which comprises a base plate 1 on which is mounted a frame 2. This frame 2 comprises a vertical arm 3, of horseshoe section, as well as a horizontal plate 4. Beneath this plate 4 is mounted an electric motor 5, the shaft of which passes through the plate 4 through opening 6. The shaft of the motor 5 is extended by a vertical screw 7, located in the cavity of the vertical arm 3. The screw 7 cooperates with a nut 8 fast with a slide block 9. The block 9 is mounted fast with the arm 3 via vertical ball bearing guides 10.

Furthermore, the slide block 9 comprises an extension 11, in the form of a horizontal plate, with which the ends of plunger rods 12 of syringes 13 are made fast, for example by means of clips.

The bodies of the syringes 13 are made fast with a support 14, itself fast with the vertical arm 3. As may be seen in FIGS. 3 and 4, the syringes 13 are arranged, with respect to plate 11 and support 14, in rectangular lines and columns.

Thus, when the motor 5 is running, it moves the nut 8 along the screw 7 and may vary the distance between the plate 11 and the support 14, this enabling the plunger rods 12 to more inside the bodies of the syringes.

All these elements are contained in an enclosure 15 comprising an opening 16 rendering accessible a mobile support 17. This support is formed by a plate adapted to serve as support, as will be seen hereinafter, for a means for filling the syringes with reagents or for a receptacled reaction assembly. The plate 17 may slide vertically due to ball-bearing guides 18 mounted on the vertical arm 3. Due to a spring 9, the plate 17 is pressed in the direction of syringes 12,13.

A window 20 made in the enclosure 15 enables the relative positions of the rods 12 in the bodies 13 of the syringes to be monitored in order to determine the amounts contained in said syringes.

FIG. 6 illustrates an embodiment of syringes 12,13. The syringe body 13 is composed of a tube, for example made of stainless steel, in which a rod 12, also made of stainless steel, may slide with slight friction. In its upper part, the rod 12 comprises a head 21 serving to make it fast with the mobile plate 11. In its lower part, the rod 12 comprises an annular recess 22 in which is housed an O-ring 23. The O-ring 23 ensures the seal between the tube 13 and rod 12. In the lower part of the tube 13, the needle of the syringe is formed by a tube 24 of smaller diameter, coaxial with tube 13. The seal between the tubes 24 and 13 is ensured by an electrically insulating sealing material 25.

Figure 8:
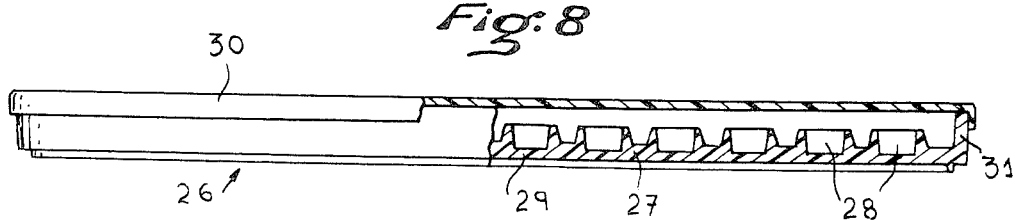
FIG. 8 is a side view, partly in section, of the receptacled assembly of FIG. 7 provided with its lid.

FIGS. 7 and 8 show a reaction assembly adapted to be used with the dispenser of FIGS. 1 and 2. This assembly is formed by a plate 26 made of transparent synthetic material, the bottom 27 of which is provided with a plurality of receptacles 28 arranged in lines and columns in the same manner as the syringes 12, 13, so that one receptacle 28 corresponds to each of said syringes. The bottom of each receptacle 28 is formed by a flat disc 29. It is therefore possible to examine what is happening in each receptacle 28 by observation from the outside through said bottoms 29. Each receptacle 28 is substantially cylindrical in form.

A lid 30 may fit on the peripheral edges 31 of the plate 26, thus closing said reaction assembly.

Figure 9:
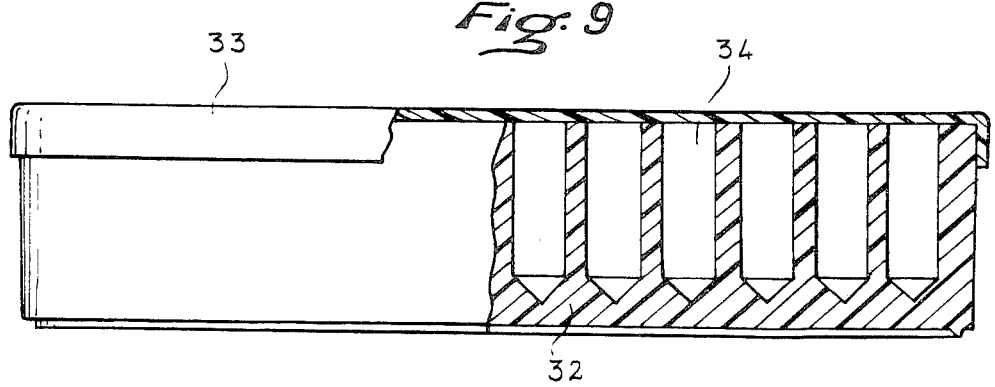
FIG. 9 is a side view, partly in section, of the means for filling the syringes of the dispenser of FIG. 2, with reagents.

FIG. 9 shows a means for filling the syringes 12,13 with reagents. This means is formed by a thick plate 32 which may be closed by a lid 33 fitting thereon. Said plate 32 is provided with receptacles 34, deeper than the receptacles 28, and arranged in the same pattern as illustrated in FIG. 7 for receptacles 28.

Due to its lid 33, the filling means 32 may serve to package reagents, each of the receptacles 34 comprising a reagent which is different from, or the same as, that of the other receptacles depending on the tests to be made. The device according to the invention functions in the following manner. The syringes 12, 13 being empty and clean, and the plate 11 being brought into its lowest position due to the action of motor 5, a plate 32 is placed on the support 17, by slightly compressing the spring 19, so that each of the needles 24 of the syringes may penetrate one receptacle 34. At this moment, the motor 5 is used to raise plate 11, causing the reagents to be drawn from the receptacles 34 into the syringes 13. The syringes 13 are therefore filled with reagents. The assembly 32 is removed from its support 17 and is replaced by a reaction assembly 26 which is arranged so that each of its receptacles 28 is located plumb with a syringe needle 24. The motor 5 is then actuated so that it turns by one step, causing the descent of the plate 11 and the dispensing into each of the receptacles 28 of a microdoses (e.g. a few fractions of microlitres to a few microlitres) of the reagents contained in the syringes 13.

Of course, the functioning of the motor 5 for lowering the plate 11 is step-by-step, whether it originates from the very structure of the motor or from an auxiliary circuit. In the reverse direction (corresponding to the filling of the syringes 12,13), the functioning of the motor 5 may be continuous. Of course, end of stroke contacts enable the amplitude of the displacement of the nut 8 to be limited.

The receptacles 28 are filled with liquids to be tested, either prior or subsequent to the filling by means of reagents. The said liquids to be tested are placed in the receptacles 28 either by means of a dispenser similar to that of FIGS. 1 and 2, or by any other means.

When the reactions occurring in the receptacles 28 have been subjected to the suitable conditions of temperature, time, etc. . . . the reaction assembly 26 is brought to an optical reading apparatus (not shown) enabling the result of these reactions to be examined through the bottoms 29 of said receptacles. The image of these reactions is possibly projected onto a video screen, with simultaneous digital display of said results.

FIG. 10 illustrates the manner in which the presence of air inside the syringes 13, near the needles 24, may be detected. To this end, a slight potential difference is applied between the bodies 13 and the needles 24, by means of a source 35. Since the sealing material 25 is electrically insulating, the passage of the current between the tube 13 and the needle 24 is effected via the contents of said syringe. When an air-bubble 36 is located near the needle 25, the electrical resistance to the passage of the current varies and it is possible to detect the presence of this bubble by measuring the variation in conductivity. To measure this variation in conductivity, there is provided a printed circuit 37 whose insulating face is applied against the tube 13 and which comprises printed conductors 38 in electrical contact with the needle 24 by means of elastic portions 39. Due to the conductor 38, the potential of the needles 24 may be brought to a measuring apparatus and the filling of the syringes 13 with reagents may therefore be monitored.

The device according to the invention is adapted to be used for making different tests automatically. It is therefore important that the positions of the reaction assembly 26 and the filling means 32 opposite the syringes 12, 13 be strictly determined and that there be no possibility of error. This may be effected by means of locating pins provided on assemblies 26 and 32 which cooperate with other pins provided on support 17.

What is claimed is:

1. A device for examining a plurality of microdoses of liquids by means of a plurality of reagents, comprising in combination:
   a frame;
   a plurality of vertical syringes mounted on said frame and arranged in a fixed pattern, each of said syringes comprising a syringe body and a piston rod;
   first means for imparting a relative vertical motion between the plurality of syringe bodies and the plurality of said piston rods, said first means being able to relatively move said syringe bodies and said piston rods between a near position and a remote position and vice versa as well as to a location between the near and remote positions, in order to draw up and dispense doses of liquids;
   a support mounted on said frame and disposed below said plurality of vertical syringes;
   second means for imparting a relative vertical motion between said plurality of syringe bodies and said support, said second means being able to relatively move said syringe bodies and said support between a near drawing up or dispensing position and a remote position;
   first plate means, for filling said syringes with reagents, provided with a plurality of receptacles adapted to contain said reagents and arranged in a fixed pattern corresponding to the pattern of said syringes, said first plate means being adapted to be detachably supported by said support; and second plate means provided with a plurality of reaction receptacles and arranged in a fixed pattern corresponding to the pattern of said syringes, said second plate means being adapted to be detachably supported by said support.

2. A device according to claim 1, wherein:
the syringe bodies are secured to the frame;
the piston rods are secured to a carriage mounted on said frame for a vertically reciprocal sliding motion; and
the support is vertically movable.

3. A device according to claim 2, wherein said carriage is moved under the action of a step-by-step electric motor actuating a vertical screw, said screw cooperating with a nut mounted on said carriage.

4. The device of claim 1, wherein the syringes of the microdose dispenser are composed of a plunger constituted by a rod provided with an annular groove in which is disposed an O-ring serving as a seal with the body of the syringe, which is formed by a tube, the needle itself being constituted by a concentric tube of smaller diameter, and the seal between the syringe body and the needle being ensured by means of a sealing material.

5. The device of claim 4, wherein the body and needle of the syringes are made of an electrically conducting material, whilst the seal between the syringe body and the needle is ensured by means of an electrically insulating material.

6. The device of claim 5, further comprising means for applying a potential difference between said bodies and said needles, a printed conductor adapted to measure the electrical potential of said needles and means for detecting, from the potential of said printed conductors, the variations in conductivity of the contents of the syringes near said needles.

7. The device of claim 1, wherein the means for filling the syringes with reagents also serves to package said reagent and comprises to this end a lid which hermetically covers it to close the receptacles.

* * * * *